(12) United States Patent
Keller et al.

(10) Patent No.: US 11,858,218 B2
(45) Date of Patent: Jan. 2, 2024

(54) TUBE SEAL AND CUT DEVICE

(71) Applicant: INVETECH, INC., San Diego, CA (US)

(72) Inventors: Cameron Keller, Carlton (AU); Robert Alister Neil, Wantirna (AU)

(73) Assignee: Invetech, Inc., San Diego, CA (US)

( * ) Notice: Subject to any disclaimer, the term of this patent is extended or adjusted under 35 U.S.C. 154(b) by 123 days.

(21) Appl. No.: 17/439,899

(22) PCT Filed: Mar. 19, 2020

(86) PCT No.: PCT/US2020/023576
§ 371 (c)(1),
(2) Date: Sep. 16, 2021

(87) PCT Pub. No.: WO2020/191168
PCT Pub. Date: Sep. 24, 2020

(65) Prior Publication Data
US 2022/0176640 A1    Jun. 9, 2022

Related U.S. Application Data

(60) Provisional application No. 62/820,372, filed on Mar. 19, 2019.

(51) Int. Cl.
*B29C 65/00* (2006.01)
*B29C 65/20* (2006.01)
*B29C 65/74* (2006.01)

(52) U.S. Cl.
CPC ............ *B29C 65/20* (2013.01); *B29C 65/743* (2013.01); *B29C 66/0044* (2013.01); *B29C 66/81425* (2013.01); *B29C 66/8322* (2013.01)

(58) Field of Classification Search
CPC ....... B29C 65/18; B29C 65/227; B29C 65/24; B29C 65/242; B29C 66/81; B29C 66/814; B29C 66/9145
(Continued)

(56) References Cited

U.S. PATENT DOCUMENTS

| 3,191,356 A | 6/1965 | Seymour et al. |
| 3,574,039 A | 4/1971 | Feht et al. |

(Continued)

FOREIGN PATENT DOCUMENTS

| EP | 1116574 | 7/2001 |
| EP | 1837161 | 9/2007 |

OTHER PUBLICATIONS

International Search Report for corresponding application No. PCT/US20/23576 dated Jun. 17, 2020.
(Continued)

*Primary Examiner* — James D Sells
(74) *Attorney, Agent, or Firm* — Lerner David LLP

(57) ABSTRACT

A tube seal apparatus including a sealing iron having a tube sealing end, an insulating shroud having a tube clamping end, wherein the sealing iron is at least partially disposed within the insulating shroud. The apparatus further includes an anvil having a cutting detail and a non-stick membrane disposed between the anvil and the tube clamping end of the insulating shroud. The sealing iron and insulating shroud are configured to advance towards a tube to be sealed positioned between the non-stick membrane and the anvil. The tube clamping end is configured to clamp the tube through the non-stick membrane. The sealing iron is configured to advance towards the tube to melt and seal the tube against the cutting detail through the non-stick membrane.

11 Claims, 6 Drawing Sheets

(58) Field of Classification Search
USPC .......................................................... 156/515
See application file for complete search history.

(56) References Cited

U.S. PATENT DOCUMENTS

| | | |
|---|---|---|
| 4,341,056 A | 7/1982 | Leanna et al. |
| 4,881,360 A | 11/1989 | Konzal et al. |
| 5,326,416 A | 7/1994 | Perrett |
| 6,719,867 B1 | 4/2004 | Mileti et al. |
| 7,115,086 B1 | 10/2006 | Campbell, Jr. |
| 11,045,853 B2 * | 6/2021 | Vilaca ..................... B21C 37/06 |
| 2004/0256058 A1 | 12/2004 | Irwin et al. |

OTHER PUBLICATIONS

European Search Report for corresponding application No. 20774108.3 dated Nov. 3, 2022.

* cited by examiner

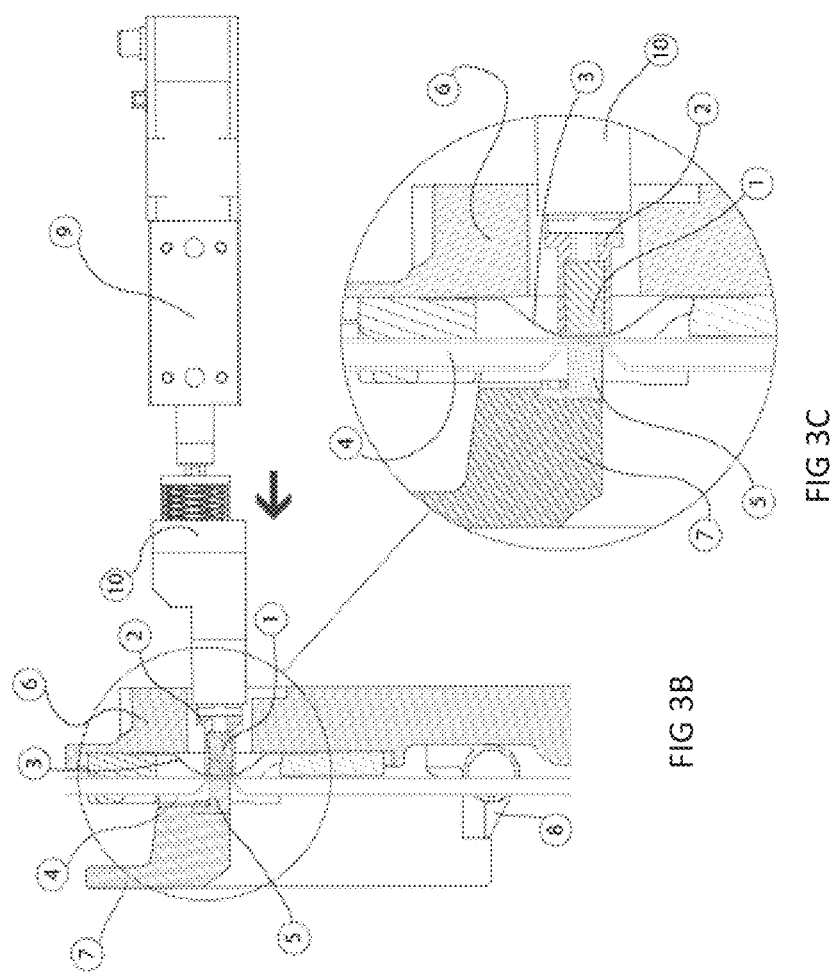

TUBE SEAL AND CUT DEVICE

CROSS-REFERENCE TO RELATED APPLICATION

This application is a 371 National Stage of International Application No. PCT/US20/23576, filed Mar. 19, 2020, which was published as International Publication No. WO 2020/191168, and which claims the benefit under 35 U.S.C. § 119(e) of the earlier filing date of U.S. Provisional Patent Application No. 62/820,372 filed on Mar. 19, 2019, the disclosures of which are incorporated by reference herein.

BACKGROUND

Embodiments of the disclosure relate to equipment for use in bioprocessing, cell therapy and regenerative medicine manufacturing. This equipment is designed to automate and control various processes that are required, typically using valves, pumps and other devices to manipulate and process various media within a functionally closed disposable set. The equipment most usually operates in clean rooms inside a pharmaceutical manufacturing facility.

For many of the processes, there is a requirement to aseptically seal and separate tubes to isolate media, product, QC (quality control) sample or simply to breakdown larger, more complex sets into smaller sub-sets for easier management and preparation for disposal.

BRIEF DESCRIPTION OF THE DRAWINGS

The invention will now be described with reference to the accompanying drawings which illustrate a non-limiting example of embodiment thereof, in which:

FIG. 3B is a cross-sectional view of the tube seal and cut device of FIG. 3A in the seal and cut position.

FIG. 3C is a detail view of FIG. 3B.

DESCRIPTION

Figure 1A:
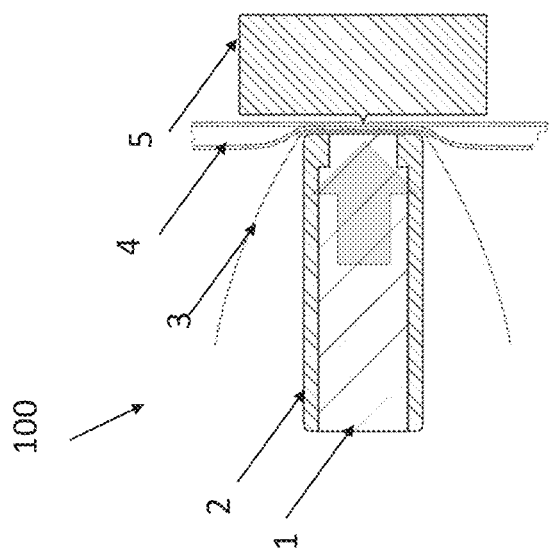
FIG. 1A is sectional view of a tube seal and cut device in a starting position according to a non-limiting example of an embodiment thereof.

There are significant benefits and risk reduction that can be realised by automating the sealing and cutting of the tubes. Equipment available to perform the task of sealing and aseptic disconnection have a range of shortcomings, including:

expensive (i.e. capital outlay and/or consumables per cut (e.g. aseptic disconnection devices, crimp sleeves, Clipster® aseptic tube disconnection system);
time consuming to operate or apply,
hazardous (e.g. crimp sleeve cutter, cut crimp sleeve producing sharp corners often seeing need for fitting of additional protective cover component);
require significant length of tube and/or room around tube to operate equipment and produce seal and achieve disconnection;
require services for non-manual/non-battery-operated devices (AC power, compressed air) for otherwise portable devices;
restrictions on tubing material (i.e. RF (radio frequency) sealer only works on tubes containing polar material e.g. PVC, EVA);
restrictions on tubing dimensions (i.e. outer diameter and wall thickness) ability to seal reliably and safely on fluid filled tube (e.g. RF tube sealer can arc when sealing fluid-filled tubes, grounding to fluid in tube resulting in pin hole in tube wall).

The potential benefits of embodiments of the disclosure especially when integrated into a piece of equipment can address several shortcomings of many of the current tube seal and cut options available. Benefits include:

reliable seal and cut process providing consistent seals and separation of the tubing without the need for scissors or other sharps (that are often used to separate sealed tubes but pose a special risk to operator with opportunity for biohazardous contamination);
ability to perform seal and cut operation on a range of different tube materials and sizes with changes to operating parameters and minor reconfiguration;
relatively quick seal and cut cycle time;
integrated into platform with required safeguards protecting operator;
tight integration of tube seal and cut equipment allowing shortest possible tubing lengths. This allows most compact and cost-effective disposable set and in some situations, can result in reduced media losses (i.e. waste) and highest performance (i.e. fluid delivery control/dispense accuracy);
automation minimising need for operator interaction;
no significant cost per seal and cut (as is the case with techniques using consumable), Accordingly, embodiments of the disclosure incorporate the improved tube seal and cut device into this prior art equipment. These embodiments achieve rapid seal and cut cycle time whilst maintaining robust and reproducible seals and cuts. These embodiments also systematically avoid exposing the operator to heat hazard and breach of the tubing which are risks with some of the current disconnection methods and can leads to process leakage and possible product or even batch loss Electrically heated sealing irons are often used to seal tubing formed from thermoplastic materials. Typically, the sealing irons have a non-stick coating to avoid having the tube material stick to the iron and leaving a residue. Where such devices are used for tube-sealing, they are also manually operated. This requires the person operating to have the dexterity and vision to load and unload the tubing and peel it off the iron in the case where the tubing sticks slightly, and to ensure there is either no residue or to remove the same so as to not adversely impact subsequent welds. In addition, for seal integrity and operator safety, current technology is limited to a relatively long cycle time (i.e. multiple minutes) as the unit can only heat up, seal and cool down with the unit latched closed.

Embodiments also incorporate a cutting detail on an anvil that opposes the sealing iron. This feature is used in impulse and RF (Radio Frequency) sealers used for tubes. The idea is that the tubing material melts and flows, thinning to the point where the tubing material is cut through but with adjacent surfaces ensuring the seal is fully established. Thus, the cut or separation point is achieved aseptically with internal surfaces of the tube (and contents) never being exposed to the outer surface.

In the disclosed embodiments, the anvil or seal back-up is attached to a door that is hinged out of the way to allow disposable set loading, but then latched closed ensuring that the tube location and anvil geometry are correctly established. In addition, the door is interlocked to ensure the operator cannot gain access to heat or pinch point hazards whilst tube seal and cut operation occurs.

The disclosed embodiments:
- carry out tube seal and cut operation by clamping a heated sealing iron against a tube through a non-stick membrane which helps to avoid tube sticking following the cut and seal operation;
- retract the sealing iron (after optimal seal and cut parameters have been executed (i.e. time, force & temp) allowing short seal and cut cycle time and allowing access by an operator without excessive delay for required manual interaction and without access/exposure to heat and pinch hazards;
- keep the sealing iron at optimum temperature without operator having access/exposure to heat and pinch hazards.

The membrane is thin and flexible, which allows it to adapt and contort to the shape of the sealing iron (and surrounding insulating shroud). The fact that the membrane is non-stick enhances the seal and cut with adequate release properties to avoid tube sticking, and aids unloading (automated or manual) following the seal and cut cycle. In terms of equipment design and suitability for cleanroom installation/operation, the membrane also serves to isolate the heater and associated actuating and other mechanisms that might otherwise pose a clean/cleanable design challenge. The membrane becomes the surface that the operator is faced with and required to keep clean and maintain, which provides another significant benefit.

Embodiments of the disclosure have the iron pre-heated to a temperature that conducts through the thin membrane material quickly to cause requisite melting and then retract the iron after the cut or tube separation is fully established. These aspects underpin the relatively rapid cycle time that can be routinely achieved and required to maximise productivity benefits and follow consistent, leak free seal and cut performance requirements.

Referring to FIGS. 1A-1E, a tube seal apparatus 100 according to an example embodiment of the disclosure is shown in sequence. Tube seal apparatus 100 has a heating block or tube sealing iron 1 translationally disposed in an insulating shroud 2. Sealing iron 1 has a sealing end 12 having a stepped portion at its sealing surface end. Insulating shroud 2 has a tube clamp end 14 having a narrowed portion corresponding to the stepped portion of sealing end 12. A seal back up or anvil 5 is disposed at the tube clamp end 14 of insulating shroud 2 and is attached to a rigid reaction surface limiting finger access by operator or safety-interlocked door (not shown in FIGS. 1A-1E). Anvil 5 has a small tube cutting detail 16 on anvil 5 facing tube clamp end 14 of insulating shroud 2. Cutting detail 16 may be configured as a raised portion that causes thinning of the tubing material after sealing has already been established in this section of tubing. This allows ready separation of the tube ends by operator with minimal to no pulling or peeling force required to disconnect newly established sealed tube ends and without the need for tools or sharps and without posing a risk of tube seal breaching. A non-stick membrane 3 is disposed between the tube clamp end 14 of insulating shroud 2 and anvil 5. A tube 4 to be sealed is placed between the non-stick membrane 3 and anvil 5. Insulating shroud 2 is configured to operate in a reciprocating fashion towards and retracted away from anvil 5. Sealing iron 1 is configured to operate in a reciprocating fashion advanced towards and retracted away from anvil 5 and also configured to move relative to insulating shroud 2. Sealing iron 1 and insulating shroud 2 may be reciprocated using mechanisms as discussed below with reference to FIGS. 3A-3C.

FIGS. 1A-1E depict the tube seal and cut sequence. Referring to FIG. 1A, the starting position is shown with insulating shroud 2 and sealing iron 1 fully retracted from anvil 5.

Figure 1B:
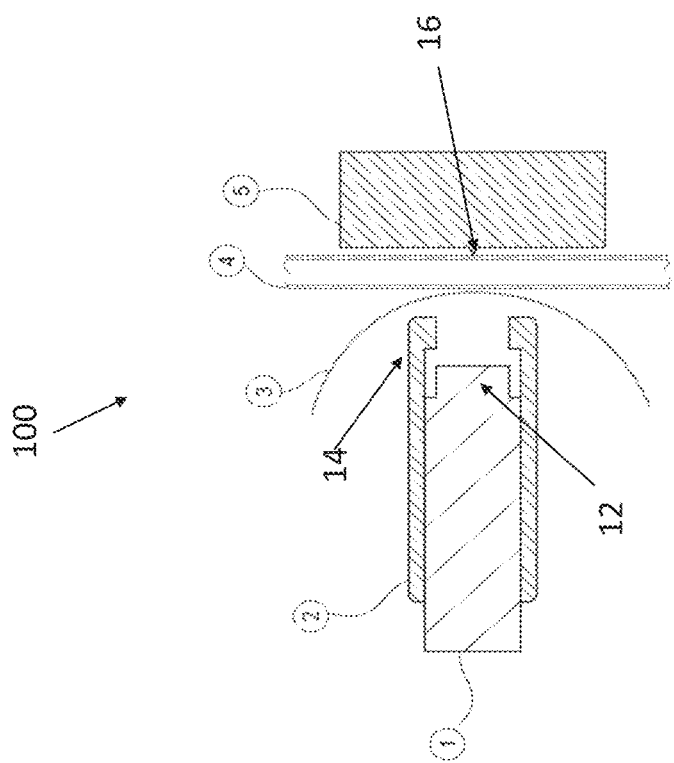
FIG. 1B is the tube seal and cut device of FIG. 1A with sealing cycle commenced.

Referring to FIG. 1B the commencement of the sealing cycle is shown with insulating shroud 2 and sealing iron 1 advanced and compressing tube 4 through membrane 3 towards anvil 5.

Figure 1D:
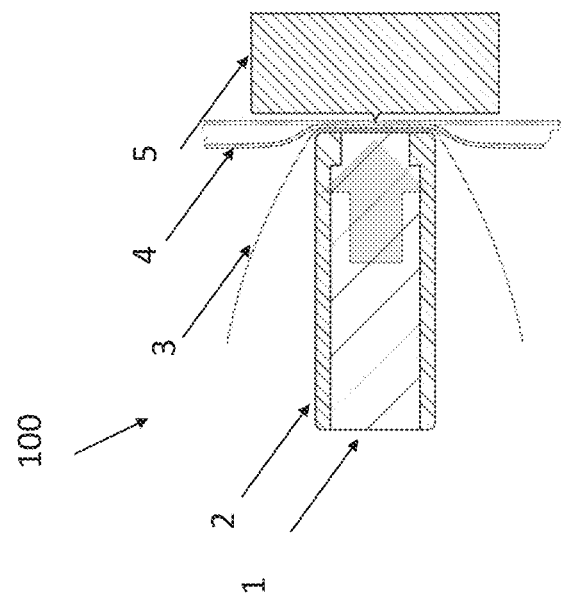
FIG. 1D is the tube seal and cut device of FIG. 1A with seal consolidating and cut (or tube thinning to point where easily separated) commencing.
Figure 1C:
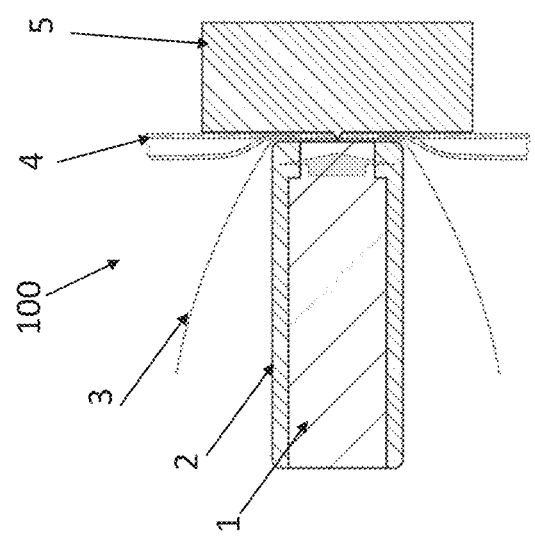
FIG. 1C is the tube seal and cut device of FIG. 1A with seal initiated.

Referring to FIG. 1C, a further development of the sealing cycle is shown wherein insulating shroud 2 and sealing iron 1 are further advanced and compress tube 4 through membrane 3 against cutting detail 16 on anvil 5, and wherein the material of tube 4 is melted and sealed with sealing iron 1 maintaining pressure. Material flows away from cutting detail 16 as sealing iron 1 comes into contact with cutting detail 16 through membrane 3 to cut through tube 4.

Referring to FIG. 1D, a seal and cut consolidating position is depicted wherein tube material solidifies with sealing iron 1 retracted. In this configuration, insulating shroud 2 remains forward and clamped against tube 4 as tube material solidifies to ensure the seal remains established, especially for tubing material with high stiffness and restoration forces that could cause the seal to be breached or otherwise compromised during short solidification period.

Figure 1E:
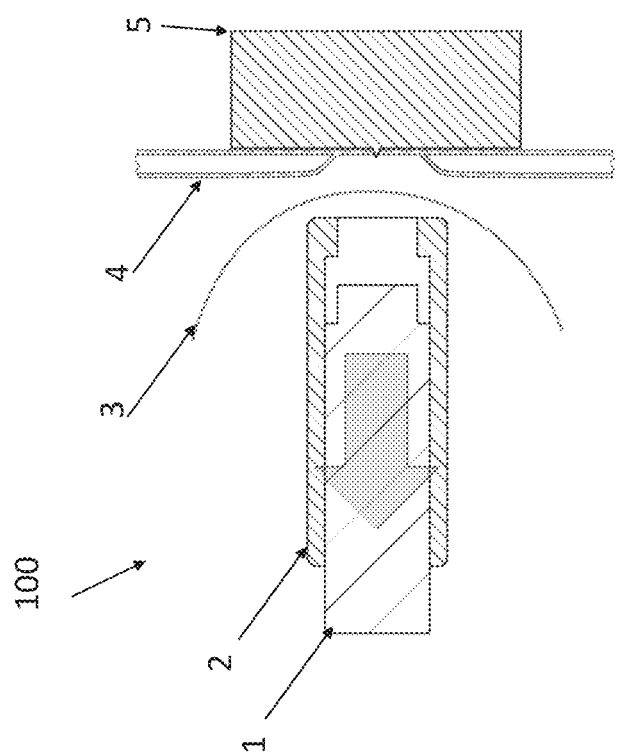
FIG. 1E is the tube seal and cut device of FIG. 1A with seal and cut or separation completed.

Referring to FIG. 1E, a seal and cut completed position is depicted wherein insulating shroud 2 and sealing iron 1 are both retracted away from anvil 5 and wherein tube 4 has been sealed and cut or separated into two separate pieces allowing disconnection of the tube and connected items on either side of the newly established cut or separation point from each other, The insulating shroud 2 helps to reduce energy usage due to radiating and convective losses. In this configuration it also plays an important role in clamping the tube 4 and providing a temperature gradient that limits the melt boundary in the tube 4, especially for thin wall tubing and stiff tubing where the restoring forces could otherwise result in stress at molten transition that would likely cause a breach in the tube wall. This Insulating shroud 2 clamps the tube 4 to isolate the transition from a flat, clamped tube to its natural circular state from the high temperature/melting zone. It thereby serves to provide the necessary margins for a more robust seal, especially on thin-wall (e.g. 0.5 mm or less) tubing. In addition, if the tube 4 being sealed is fluid filled, insulating shroud 2 serves to help occlude the fluid and push it out of the seal and high temperature zone, helping avoid high temperature exposure of the fluid. This reduces possible boiling and excess pressure generation by fluid/generated gas that might cause a rupture of molten tube wall during the sealing process. Depending on the application, there may also be residual or induced tension on the tube 4. Since insulating shroud 2 is configured as a clamp, it could also serve to isolate the tension and avoid the seal being compromised by tube 4 remaining under tension that could otherwise quite easily lead to elongation or stretching of molten section of tube leading to a seal or tube wall breach.

Figure 2:
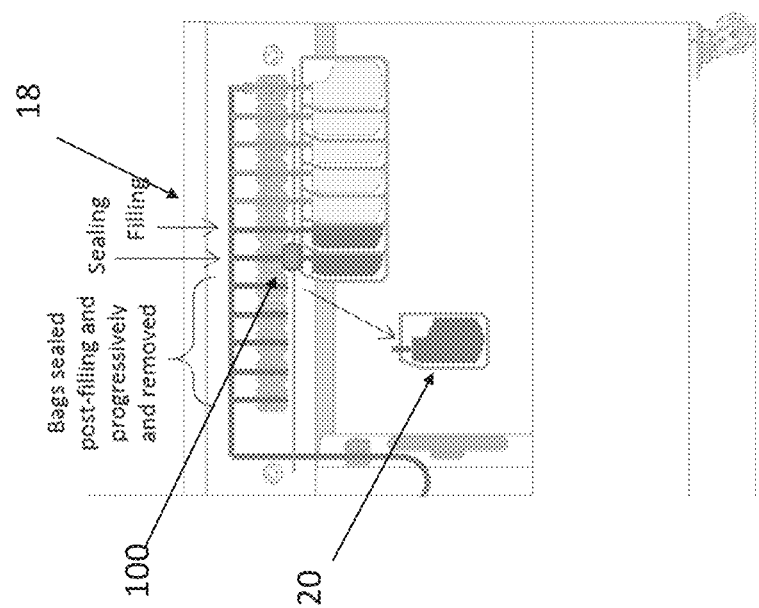
FIG. 2 is a schematic view of tube seal and cut device in a bag filler application.

In terms of the integration of this tube seal apparatus 100, it may be utilised in various configurations to support sealing and cutting of different tubing materials and wall thickness. On a bag filler where there are a number of bags in a row, a door may cover all of the bags and fill tubes with continuous or individual anvils backing up each tube but with a traversing sealer. In this respect, a single sealer would help provide uniformity in terms of force and temperature to each of the tubes it was accessing and overall, if servicing multiple positions, considerably reducing cost and complexity of the equipment control system by avoiding having multiple sealing heads. Also, with a bag filler embodiment, the bags are often sequentially filled and having a single, traversing device means tube cutting and sealing can happen directly following bag filling and whilst next bag is being filled. In this way, productivity is maximised by avoiding seal and cut at the conclusion of all bags being filled. Instead, this invention could make bags available for more timely removal and subsequent processing sequentially and directly after completion of the tube seal and cut process. Referring to FIG. 2, a bag filler application 18 is depicted indicating progressive filling of bags 20 by tubes 4, sealing and cutting by tube seal apparatus 100 and then bag 20 removal.

Figure 3A:
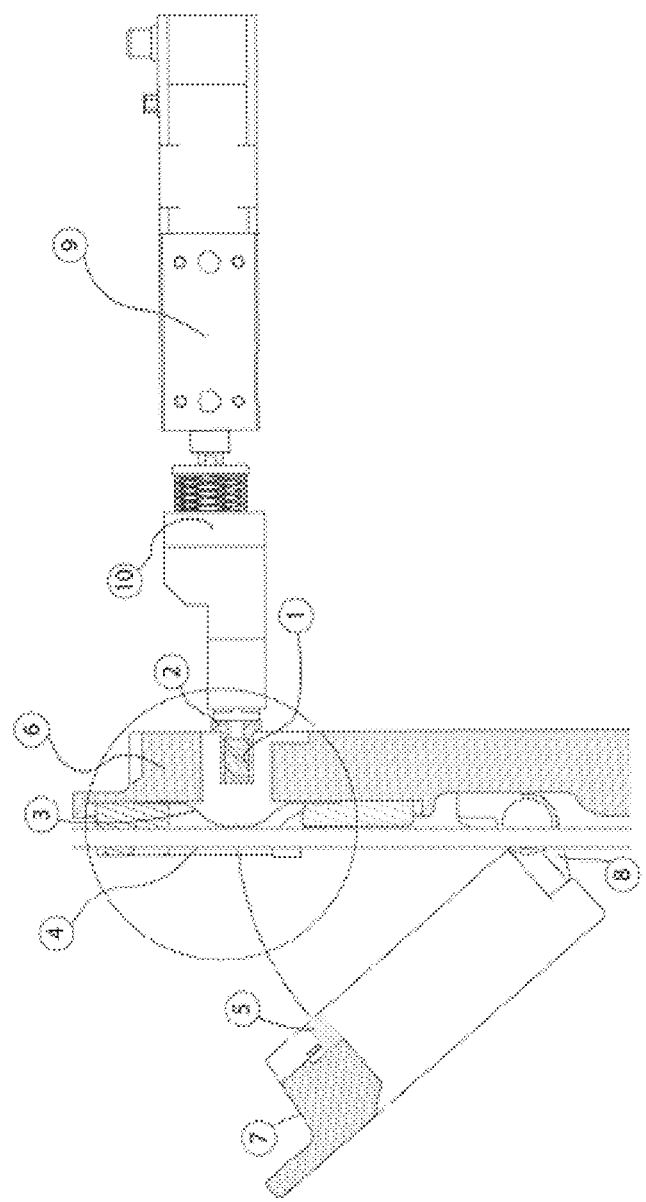
FIG. 3A is a cross-sectional view of another example embodiment of a tube seal and cut device in a standby/tube loading position with the door in an open position.

Referring to FIGS. 3A-3C, another example embodiment. This embodiment incorporates many of the features described in the previously described embodiments. In this embodiment depicted here, the iron 1 and shroud 2 do not move relative to one another and are moved together, and their sealing end and tube clamp end, respectively do not have corresponding narrowed features.

Referring to FIG. 3A, a tube seal and cut device is shown in standby position ready for set/tube 4 loading. The membrane 3 is fixed to a membrane holder on chassis 6 where a 3" (75 mm) wide web or strip of membrane film that is clamped into a holder which helps form/achieve the required convex 2D profile. This membrane holder is removable from the platform for membrane replacement and maintenance if required.

A typical example of where this seal and cut device would be used is where bags need to be aseptically sealed and separated after being filled with a desired volume of fluid. In this instance, the disposable set including bags and fill tubes would be loaded on to the system with the tube section to be sealed and cut running in front of the membrane 3 in the required location and then the door 7 would be closed over the tube 4, bringing the anvil 5 into position.

Referring to FIGS. 3B and 3C, the tube seal and cut system is shown in the sealing position. Continuing the bag filling example, following filling of the bag, the heated sealing iron 1 assembly is actuated forward, pushing the tube 4 against the anvil 5 through the non-stick membrane 3, resulting in sealing and cutting/separation of the tube 4 as outlined above with respect to FIGS. 1A-1E. The mechanism used to motivate/actuate the components actively participating in the sealing function may be a pneumatic cylinder and electric actuator or, as shown in the figures, a guided ball screw actuator with electric motor assembly 9 which moves a sealing iron 1 assembly carrier 10. Force control with the ability of the sealing iron assembly to maintain force by moving forward during the sealing operation as the tube melts and flows is an important and beneficial aspect of this system to achieve reproducibility. This could also be achieved using a guided pneumatic cylinder (for pneumatically actuated system). For the electric actuator, force control can be achieved using torque (i.e. motor current) control or with alternative embodiment using spring loaded head with variable positioning (i.e. stroke) controlling the force applied during the sealing operation.

At the conclusion of the sealing cycle, the heated sealing iron 1 assembly is retracted backward away from the membrane 3 and anvil 5 and seeing the molten tube 4 material solidify to complete the seal and cut detail. This sealing process might be repeated several times, traversing to allow sealing and separating of a multitude of adjacent tubes 4. At the conclusion of the process, the door 7 is opened and the filled, sealed and separated bags removed for subsequent processing (labelling, packaging, freezing, etc.).

Exemplary parameters for operation are as follows:

Iron temperature: working range=100° C.→200° C. typical sealing range dependent on tubing. Nominal setting=160° C. Possible high temperature of 350° C. for intermittent operation.

Iron contact time: working range=6→>30 sec, dependent on tubing.

Iron pressure/force: working range=80 N→200 N. Nominal setting=120 N.

The iron 1 may be comprised of aluminium or other suitable thermally conductive materials. The shroud 2 and anvil 5 may be comprised of a polyether ether ketone (PEEK) or other suitable materials with high continuous working temperature capability. The non-stick membrane 3 may be comprised of PEEK or polyimide film or other suitable materials that are suitably thin and flexible to allow heat to be readily conducted through it from sealing iron assembly to tube whilst also having ability to withstand process temperatures intermittently without degradation.

Features of the disclosed embodiments may be combined, rearranged, omitted, etc., within the scope of the invention to produce additional embodiments. Furthermore, certain features may sometimes be used to advantage without a corresponding use of other features.

Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

What is claimed is:

1. A tube seal apparatus comprising:
   a sealing iron comprising a tube sealing end;
   an insulating shroud comprising a tube clamping end, wherein the sealing iron is at least partially disposed within the insulating shroud;
   an anvil comprising a cutting detail; and
   a non-stick membrane disposed between the anvil and the tube clamping end of the insulating shroud;
   wherein the sealing iron and insulating shroud are configured to advance towards a tube to be sealed positioned between the non-stick membrane and the anvil; wherein the tube clamping end is configured to clamp the tube through the non-stick membrane; and wherein the sealing iron is configured to advance towards the tube to melt and seal the tube against the cutting detail through the non-stick membrane.

2. The tube seal apparatus of claim 1, wherein the sealing iron and insulating shroud are configured to retract away from the sealing membrane after sealing the tube.

3. The tube seal apparatus of claim 2, wherein the sealing iron and insulating shroud are configured to move together when retracting away from and advancing towards the sealing membrane.

4. The tube seal apparatus of claim 2, wherein the sealing iron and insulating shroud are configured to move relative to one another when retracting away from and advancing towards the sealing membrane.

5. The tube seal apparatus of claim 2, wherein the anvil is mounted on a door configured to be openable to allow loading of the tube between the anvil and non-stick membrane.

6. The tube seal apparatus of claim 1, wherein the tube sealing end of the heating iron is stepped, and the clamping end of the insulating shroud has a narrowed portion corresponding to the stepped portion.

7. The tube seal apparatus of claim 1, wherein the cutting detail is configured as a raised portion which causes thinning of the tube material.

8. The tube seal apparatus of claim 1, wherein the non-stick membrane comprises one of polyether ether ketone (PEEK) and polyimide film.

9. The tube seal apparatus of claim 2, wherein the sealing iron is configured to have a temperature between 100° C. and 200° C. when advanced towards the sealing membrane.

10. The tube seal apparatus of claim 2, wherein the sealing iron is configured to contact the sealing membrane between 6 and 30 seconds.

11. The tube seal apparatus of claim 2, wherein the sealing iron is configured to contact the sealing membrane at a force between 80 N and 200 N.

* * * * *